United States Patent [19]

Interrante

[11] 4,434,103
[45] Feb. 28, 1984

[54] SUBSTITUTED SILICON-OXYGEN-ALUMINUM OLIGOMERS AND PREPARATION THEREOF

[75] Inventor: Leonard V. Interrante, Schenectady, N.Y.

[73] Assignee: General Electric Company, Schenectady, N.Y.

[21] Appl. No.: 303,447

[22] Filed: Sep. 18, 1981

[51] Int. Cl.³ ............................................. C07F 5/06
[52] U.S. Cl. ........................... 260/448 B; 106/287.13; 106/287.17; 528/26; 528/27; 528/30
[58] Field of Search ............... 260/448 B; 106/287.13, 106/287.17; 528/26, 27, 30

[56] References Cited

U.S. PATENT DOCUMENTS 3,061,587 10/1962 Rust et al.
3,299,109 1/1967 Sander .................... 260/448 B X
3,578,619 5/1971 Reeder .................... 260/448 B X
3,657,149 4/1972 Vandenberg.
3,657,159 4/1972 Vandenberg.

OTHER PUBLICATIONS

Andrianov, Polymers With Inorganic Main Chains, U.S. Dept. of Commerce, Office of Technical Services Wash. D.c. pp. 575-592, (1963).
Synthesis and Mechanical Properties of Stoichiometric Aluminum Silicate (Mullite), Mazdiyasni et al, Journal of the American Ceramic Society, vol. 55, no. 11 (1972).
Synthesis of New Polymers with Inorganic Chains of Molecules, Andrianov et al., Journal of Polymer Science, vol. XXX, pp. 513-524 (1958).
Preparation of Glasses and Ceramics from Metal-Organic Compounds, Yoldas, Journal of Materials Science, 12 (1977) pp. 1203-1208.
Developments in Inorganic Polymer Chemistry, Elsevier Publishing Company, New York (1962), J. Idris Jones, pp. 172-174, 200-213 and 238-251.
Organosilicon Heteropolymers and Meterocompounds, Barisov, et al, Plenum Press (1970) pp. 255-303.
Organic and Biological Chemistry, Patterson et al, Polymers Containing Chelated Aluminum, Aug. 1959, pp. 4213-4217.
The Air Force Inorganic Polymer Program, Rau, WADC Technical Report 58-160 (1958) pp. 21-25.

Primary Examiner—Helen M. S. Sneed
Attorney, Agent, or Firm—William A. Teoli; James C. Davis, Jr.; James Magee, Jr.

[57] ABSTRACT

A method is provided for applying aluminosilicate coatings onto a variety of substrates, for example, metals, metal alloys and ceramics. Certain organic solvent-soluble, organic substituted, silicon-oxygen-aluminum oligomers and method for preparing them also are provided.

4 Claims, No Drawings

SUBSTITUTED SILICON-OXYGEN-ALUMINUM OLIGOMERS AND PREPARATION THEREOF

BACKGROUND OF THE INVENTION

Prior to the present invention, it was generally known that aluminosilicate materials, for example, mullite, a naturally occurring, high temperature performance material composed essentially of chemically combined aluminum, oxygen and silicon atoms $x(Al_2O_3)\cdot SiO_2$, where x is 1.5 to 2.0, was an attractive candidate for a variety of high temperature applications. In addition, mullite, unlike closely related aluminum-oxygen-silicon materials, is known to be highly resistant to attack by strong acids and other corrosive reagents, as taught by R. F. Davis and T. A. Pask, "Mullite", pp. 37–76 in "High Temperature Oxides", Part IV, Allen M. Alper, ed., Academic Press, NY (1971). However, no technique was known for making mullite in a form, such as a high temperature, corrosion resistant, coating. It would be highly desirable, therefore, to provide a procedure whereby mullite could be made synthetically in an appropriate form to utilize its outstanding properties.

As shown by W. A. D. C. Technical Report 58-160 ASTIA document No. 155675, The Air Force Inorganic Polymer Program, R. L. Rau, (June 1958), Pages 21–25, silicon-oxygen-aluminum polymers can be made by effecting reaction between an aluminum chelate dialkoxide, for example, diisopropoxyaluminum acetylacetonate and a difunctional saline, such as dimethylacetoxysilane. Reaction was carried out in boiling toluene to produce a variety of products varying from soft resins, waxes, or powders. I have found that the aforementioned aluminum-oxygen-silicon materials of R. L. Rau provide glass-like coatings when heated at temperatures exceeding 350° C. in an oxidizing atmosphere, for example air. However, the resulting aluminosilicate coatings fall outside of the mullite composition range, and do not provide optimum coating characteristics on ceramic or metal substrates in particular applications. Additional procedures for making organoaluminosilanes are shown by S. N. Barisov et al, Organosilicon Heteropolymers and Heterocompounds, Plenum Press, New York (1970), however, none of these procedures lead to the preparation of organoaluminosilanes with Al/Si atomic ratios in the range appropriate for mullite.

H. Dislich, New Routes to Multicomponent Oxide Glasses, Angewandte Chemie, International Edition, Vol. 10, pages 383–434 (1971) has described the preparation of coherent multicomponent oxide glass coatings on various substrates using mixtures of metal alkoxides in organic solvents. Similarly, Yoldas and Partlow, Formation of Continuous Beta Alumina Films and Coatings at Low Temperatures, Ceramic Bulletin, Vol. 59, No. 6, (1980) pages 640–642, describe the preparation of continuous films of $NaAl_{11}O_{17}$ on ceramic substrates using solutions of the corresponding metal alkoxides. In both reports, removal of the organic component is effected by hydrolysis of the organometallic film after deposition and the resultant metal oxide films do not possess the desired thermal and chemical stability characteristic of mullite.

As shown by K. S. Mazdiyasni et al, Synthesis and Mechanical Properties of Stoichiometric Aluminum Silicate (Mullite), Pages 548–552, Vol. 55, No. 11, Journal of the American Ceramic Society, a method for preparing mullite is provided by reacting aluminum trisisopropoxide and silicon tetrakisisopropoxide under reflux conditions in isopropyl alcohol. The resulting alkoxide solution can be ammoniated to produce the corresponding hydroxy aluminosilicate which can be dried in vacuum to produce mullite powders. However, the aforementioned technique was unsuitable for applying a mullite coating onto various substrates.

STATEMENT OF THE INVENTION

The present invention is based on the discovery that chelated aluminum-oxygen-silicon oligomer of the formula,

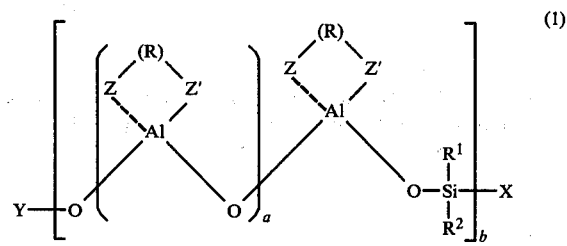

can be applied as an organic solvent soluble solution onto various substrates and thereafter heated to elevated temperatures, such as 450° C., to produce an amorphous, adherent aluminosilicate coating onto the substrate. In instances where a=2, this coating can be heated further to 1300° C. to produce a crystalline mullite phase on the surface of the substrate which substantially improves resistance to corrosion. In formula (1), Y is selected from monovalent $C_{(1-13)}$ hydrocarbon radicals and substituted $C_{(1-13)}$ monovalent hydrocarbon radicals, R is selected from divalent organic radicals, $R^1$ and $R^2$ are selected from monovalent hydrocarbon radicals and substituted monovalent hydrocarbon radicals, Z and Z' are selected from —O—, —N= and —S—, X is an acyloxy, hydroxy or halogen radical, a has an average value equal to 1 to 4 inclusive, and b has a value equal to at least 1.

In a further aspect of the present invention, there is provided a method for applying an aluminosilicate coating onto a ceramic, metal or metal alloy substrate which comprises (1) applying an organic solvent solution of an organic substituted silicon-oxygen-aluminum oligomer of formula (1), onto such substrate and (2) heating the treated substrate to a temperature in the range of from 350° C. to 1500° C. in an oxidizing atmosphere for a time sufficient to oxidize any organic material on the treated substrate.

There is also provided by the present invention, a method for making organic solvent soluble aluminum-oxygen-silicon oligomer useful for providing an alumino-silicate coating on a ceramic, metal or metal alloy substrate which comprises (A) hydrolyzing chelated aluminum alkoxide of the formula,

with water, using M moles of chelated aluminum alkoxide, where M has a value of 2 to 5, per M-1 moles of water, to produce low molecular weight alkoxy-terminated aluminum-oxygen oligomer, (B) coreacting the low molecular weight alkoxy terminated aluminum-oxygen oligomer of (A) with a sufficient amount of a difunctional organosilane of the formula,

to provide at least one X radical, per alkoxy radical of the alkoxy-terminated aluminum-oxygen oligomer, and (C) effecting the separation of volatiles from the resulting mixture, by distillation or evaporation, where R, $R^1$ and $R^2$, Y, Z, and Z' are as previously defined and X is an acyloxy, hydroxy or halogen radical.

In a further aspect of the present invention there are provided shaped ceramic, metallic, or metallic alloy substrates coated with an aluminosilicate consisting essentially of chemically combined units of the formula,

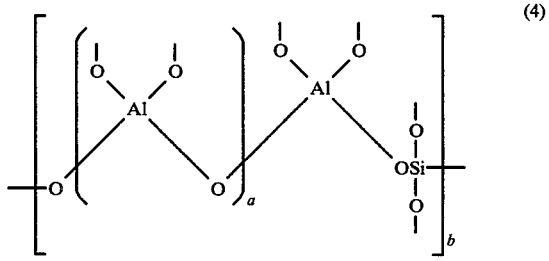

where a and b are are as previously defined.

Chelated aluminum alkoxides of formula (2) which can be utilized in the practice of the present invention are, for example

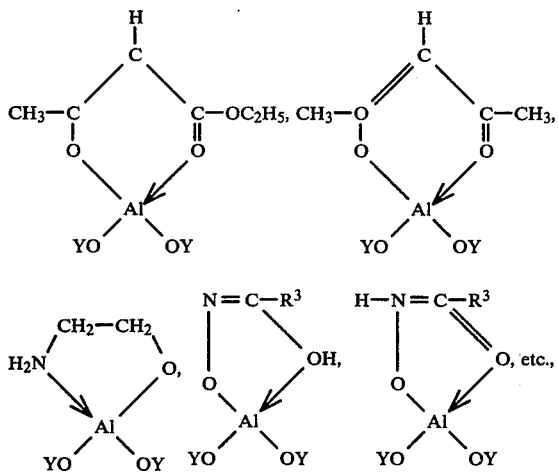

where Y is selected from $CH_3$, $C_2H_6$, $C_3H_7$, etc., and $R^3$ is selected from H, $CH_3$, $C_2H_6$, etc.

Difunctional silanes of formula (3) which can be employed in the practice of the present invention are, for example,

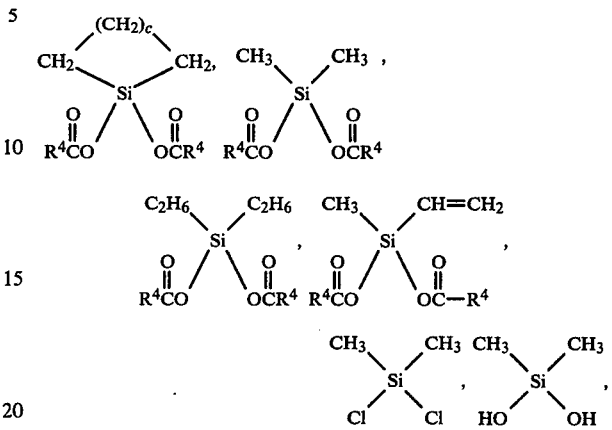

where $R^4$ is selected from H, $CH_3$, $C_2H_6$, $C_3H_7$, etc., and c is equal to 2 or 3.

Radicals included within R of formulas (1) and (2) are, for example,

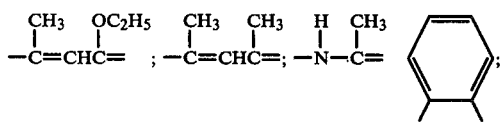

and —$CH_2CH_2$—. Radicals included with $R^1$ and $R^2$ of formula (3) are $C_{(1-8)}$ alkyl radicals, for example, methyl, ethyl, propyl, butyl, etc.; alkenyl radicals, for example, vinyl, propenyl, etc.; aryl radicals, for example phenyl, napthyl, etc. Additional $R^1$ and $R^2$ radicals are for example, cyanoethyl and trifluoropropyl.

Substrates which can be treated in accordance with the practice of the method of the present invention are, for example, fused silica, alumina, silicate glasses, titanium metal, inconel, tungsten carbide, etc.

In the practice of the present invention the chelated aluminum alkoxide of formula (2) can be hydrolyzed with an aqueous alkanol having 5 to 25% by weight alkanol. There can be used $C_{(1-8)}$ alkanols such as ethyl alcohol, methyl alcohol and propyl alcohol, etc. In particular instances glycols can also be used for example ethylene glycol, etc. Hydrolysis can be effected at temperatures of from 0° C. to 100° C. It has been found that distillation of the resulting hydrolysis mixture can be facilitated with the use of an inert hydrocarbon solvent, for example toluene to effect the removal of the alkanol and water. The resulting partial hydrolyzate can be varied in composition depending upon the amount of water utilized during the hydrolysis as previously defined.

The oligomer of formula (1) can be prepared by coreacting the partial hydrolyzate of the chelated dialuminum alkoxide with the difunctional organosilane of formula (3) in accordance with the proportions previously defined. However, it is preferred to use 1/5 to 1 mole of difunctional silane, per mole of chelated aluminum alkoxide. Reaction is preferably effected under substantially anhydrous conditions, for example, by use of an inert gas, such as nitrogen, to exclude atmospheric moisture. Temperatures of from 20° C. to 200° C. can be used with agitation, such as stirring from 5 minutes to 14 days. An inert organic solvent such as a hydrocarbon solvent, for example, $C_{(7-13)}$ aliphatic or aromatic hydrocarbon solvents, such as toluene can be used. Distillation of the mixture to effect the removal of volatiles can be effected at ordinary pressures at the boiling point of the solvent employed. If desired, reduced pressure can be employed such as from $10^{-3}$ to 750 torr to facilitate removal of volatiles.

A solution of the silicon-oxygen-aluminum oligomer of formula (1) in an inert organic solvent can be applied onto various substrates and allowed to dry in the absence of moisture. The resulting treated substrates can then be heated at a temperature in the range of from 350° C. to 1000° C. for a period of from 10 minutes or more to a few hours depending upon such factors as temperature used, nature of oligomer, etc., in an oxidizing atmosphere to form an amorphous coating on the substrate consisting essentially of chemically combined units of formula (4). The coated substrate can then be further heated to a temperature of from 1000° C. to 1500° C. to convert the alumonosilicate glass to an adherent aluminosilicate coating which contains mullite in microcrystalline form.

In order that those skilled in the art will be better able to practice the present invention, the following examples are given by way of illustration and not by way of limitation. All parts are by weight.

EXAMPLE 1

In accordance with the procedure shown by Patterson et al, Polymers Containing Chelated Aluminum, J. Amer. Chem. Soc., 81, 4213 (1959), ethylacetoacetate was reacted with aluminum trisisopropoxide. There was obtained (ethylacetoacetato)aluminum diisopropoxide which boiled at 145°–150° C. at 0.2 torr pressure. More particularly, there was reacted 130 parts ethylacetoacetate and 204 parts of aluminum isopropoxide. The identity of the resulting product was confirmed by elemental analysis.

A solution of 5.09 parts of distilled water and 50 parts of dry distilled isopropyl alcohol was added with stirring to 116.7 parts of the above aluminum chelate in 240 parts of anhydrous toluene over 50 minutes. The resulting clear solution was distilled until the isopropyl alcohol and most of the toluene was removed. Based on method of preparation there was obtained a partial hydrolyzate of ethyl(acetoacetate) aluminum diisopropoxide having the average formula,

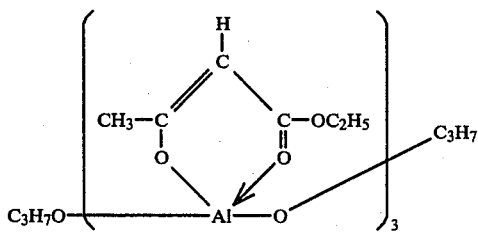

There was added a solution of 25.0 parts of diacetoxydimethylsilane in 50 parts of toluene under a nitrogen atmosphere to the above hydrolyzate while it was stirred. The addition was completed in a period of about 1 hour. The resulting reaction mixture was refluxed for 12 days under a blanket of dry nitrogen, followed by distillation of atmospheric pressure in an oil bath at 150° C. to remove the acetate ester formed plus the toluene solvent. The mixture was then heated further in an oil bath at atmospheric pressure at 165° C. for 1 day and then at 180° C. for a second day. The mixture was heated under vacuum at 125° C. for several hours, then at 180° C. for a few additional hours. There was obtained an aluminum-oxygen-silicon oligomer in the form of a glassy solid. Based on method of preparation and elemental analysis, the solid had the following average formula,

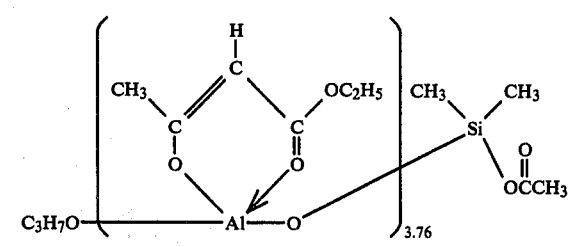

A 0.1 gram of this oligomer in an alumina crucible was heated in a thermobalance from approximately 24° C. to 1000° C. over 100 minutes in a stream of dry air flowing at 400 ml/min. The residue remaining in the crucible was examined under a microscope and found to consist of small pieces of mainly colorless transparent, glass-like solid admixed with black glass-like pieces. Electron microprobe analysis of the mixture indicated a uniform distribution of aluminum and silicon in approximately the same molar proportion (Al/Si=3.7/1) as in the original oligomer. This material was found to be amorphous to X-rays; however, after heating further in air for 2 hours at 1250°–1300° C. lines characteristic of crystalline mullite were observed in the X-ray diffraction pattern.

EXAMPLE 2

A 5% solution of the aluminum-oxygen-silicon oligomer of Example 1 in toluene was mixed with aluminum oxide fiber having lengths varying from a few microns to a few mm in a nitrogen filled dry box. There was utilized approximately 47 milligrams of aluminum oxide fiber which was treated with approximately 0.15 gram of toluene solution. The treated fibers were then placed on a fused silica plate and dried under a stream of nitrogen for 1-3 days. The plate was then heated in an oven under flowing oxygen at 450° C. for 4 hours and allowed to cool. The resulting fiber was examined under a microscope. It was found to be coated and stongly held together by a continuous, smooth, adherent film.

EXAMPLE 3

The above procedure was repeated, except that in place of the aluminum oxide fiber, there was used a corrosion test pin of Renee 80 coated with CoCrAlY. The pin had been initially rinsed with distilled water and dried for several hours in a 100° C. oven prior to being immersed in the above-described solution of aluminum-oxygen-silicon oligomer in toluene. After a second oligomer treatment in toluene, the treated pin was placed in a dessicator under flowing nitrogen gas over a period of 12 hours. The treated pin was then heated in dry air from room temperature to 900° C. in a thermobalance.

The treated pin was coated with a known amount of sodium sulfate and heated in an atmosphere containing oxygen and sulfur oxides at 750° C. for 24 hours. A weight increase would indicate evidence of corrosion. The treated pin showed a reduced weight gain as compared to an equivalent test pin free of the aluminum-oxygen-silicon coating. These results showed that the aluminum-oxygen-silicon coating resisted the effects of sodium sulfate sulfur trioxide corrosion.

EXAMPLE 4

Sliced 50×20×1 millimeter fused silica substrates were cleaned by successive washings in a 2% sodium hydroxide solution, distilled water and ethanol and dried, and then dipped into a 30% toluene solution of the aluminum-oxygen-silicon oligomer of Example 1. An analysis for metal content showed an aluminum to silicon mole ratio of 3.5.

The coated fused silica strips were heated in a furnace at a temperature of 1000° C. for 30 minutes. Microscopic examination of the coating showed no irregularities. The thickness of the coating was measured by dipsometry and was found to be 0.7 micron. Electron microprobe analysis indicated the presence of both aluminum and silicon on the surface as expected for an aluminosilicate coating. This coating was apparently unaffected by immersion of the treated substrate in 6 N hydrochloric acid.

Although the above examples are directed to only a few of the very many variables of the practice of the method of the present invention, articles obtained and the aluminum-oxygen-silicon polymers of the present invention, it should be understood that the present invention is directed to a much broader variety of such methods and materials as shown in the description preceding these examples.

What I claim as new and desire to secure by Letters Patent of the United States is:

1. A method for making organic solvent soluble aluminum-oxygen-silicon oligomers useful for providing an aluminosilicate coating on a ceramic, metal or metal alloy substrate which comprises
    (A) hydrolyzing a chelated aluminum alkoxide of the formula,

with water using M moles of chelated aluminum alkoxide, where M has a value of 2 to 5, per M-1 moles of water, to produce low molecular weight alkoxy-terminated aluminum-oxygen oligomer,
    (B) coreacting the low molecular weight alkoxy terminated aluminum oxygen oligomer of (A) with a sufficient amount of a difunctional organosilane of the formula, $$\begin{array}{c} R^1 \\ | \\ SiX_2 \\ | \\ R^2 \end{array}$$

to provide at least one X radical per alkoxy radical of the chelated aluminum oxide oligomer of (A), and
    (C) effecting the separation of volatiles from the resulting mixture, where Y is a monovalent $C_{(1-13)}$ hydrocarbon radical, R is selected from polyvalent organic radicals, $R^1$ and $R^2$ are selected from monovalent hydrocarbon radicals and substituted monovalent hydrocarbon radicals selected from the group consisting of cyanoethyl and trifluoropropyl, and X is an acyloxy, hydroxy or halogen radical.

2. A method in accordance with claim 1, where the difunctional organosilane is dimethyldiacetoxysilane.

3. An aluminum-oxygen-silicon oligomer made in accordance with the method of claim 1 having the formula,

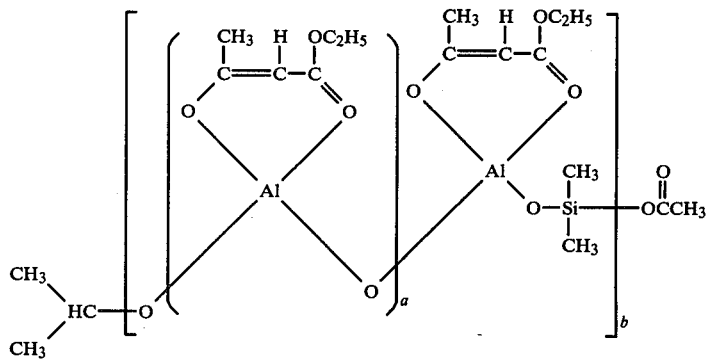

where a has an average value of 2 to 4 inclusive, and b has a value equal to at least one.

4. An aluminum-oxygen-silicon oligomer made by the methods of claim 1 having the formula,

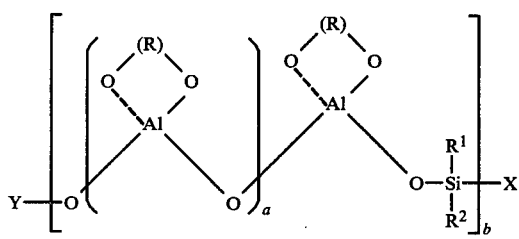

where Y is a monovalent $C_{(1-13)}$ hydrocarbon radical, R is selected from divalent organic radicals, $R^1$ and $R^2$ are selected from monovalent hydrocarbon radicals and substituted monovalent hydrocarbon radicals selected from the group consisting of cyanoethyl and trifluoropropyl, X is an acyloxy, hydroxy or halogen radical, a has an average value of 2 to 4 inclusive, and b has a value equal to at least one.

* * * * *

UNITED STATES PATENT AND TRADEMARK OFFICE
CERTIFICATE OF CORRECTION

PATENT NO.   : 4,434,103

DATED        : February 28, 1984

INVENTOR(S)  : Leonard V. Interrante

It is certified that error appears in the above—identified patent and that said Letters Patent is hereby corrected as shown below:

Column 8, line 21, cancel "selected"
Column 8, line 22, cancel "from the group consisting of cyanoethyl and trifluoro-"
Column 8, line 23, cancel "propyl" and substitute -selected from the group consisting of methyl, ethyl, propyl, butyl, vinyl, propenyl, phenyl, napthyl, cyanoethyl and trifluoropropyl- Signed and Sealed this Twenty-eighth Day of May 1985

[SEAL]

Attest:

DONALD J. QUIGG

Attesting Officer

Acting Commissioner of Patents and Trademarks

UNITED STATES PATENT AND TRADEMARK OFFICE
CERTIFICATE OF CORRECTION

PATENT NO.   : 4,434,103
DATED        : February 28, 1984
INVENTOR(S)  : Leonard V. Interrante It is certified that error appears in the above-identified patent and that said Letters Patent is hereby corrected as shown below:

Column 8, line 65, after "of", insert -methyl, ethyl, propyl, butyl, vinyl, propenyl, phenyl, naphthyl-.

Signed and Sealed this

Twenty-ninth Day of October 1985

[SEAL]

Attest:

Attesting Officer

DONALD J. QUIGG

Commissioner of Patents and Trademarks—Designate